(12) United States Patent
Talbot et al.

(10) Patent No.: US 10,285,402 B2
(45) Date of Patent: May 14, 2019

(54) USE OF 4-CHLOROINDOLE-3-ACETIC ACID FOR CONTROLLING UNWANTED PLANTS

(71) Applicant: PREMIER TECH TECHNOLOGIES LTÉE, Rivière-du-Loup (CA)

(72) Inventors: Pierre Talbot, Rivière-du-Loup (CA); Alain Bélanger, Rivière-du-Loup (CA); George Kanellos, Rivière-du-Loup (CA); Shaun Purcell, Rivière-du-Loup (CA); Paul Lefebvre, Rivière-du-Loup (CA); Geneviève Roy, Rivière-du-Loup (CA); Dominique Lequere, Rivière-du-Loup (CA)

(73) Assignee: PREMIER TECH TECHNOLOGIES LTÉE, Rivière-du-Loup (CA)

( * ) Notice: Subject to any disclaimer, the term of this patent is extended or adjusted under 35 U.S.C. 154(b) by 0 days.

(21) Appl. No.: 15/511,487

(22) PCT Filed: Sep. 15, 2015

(86) PCT No.: PCT/CA2015/050894
§ 371 (c)(1),
(2) Date: Mar. 15, 2017

(87) PCT Pub. No.: WO2016/041071
PCT Pub. Date: Mar. 24, 2016

(65) Prior Publication Data
US 2017/0258086 A1  Sep. 14, 2017

(30) Foreign Application Priority Data
Sep. 16, 2014  (CA) ..................... 2863477

(51) Int. Cl.
| A01N 43/38 | (2006.01) |
| A01N 47/28 | (2006.01) |
| A01N 55/02 | (2006.01) |
| A01N 59/08 | (2006.01) |

(52) U.S. Cl.
CPC ............. *A01N 43/38* (2013.01); *A01N 47/28* (2013.01); *A01N 55/02* (2013.01); *A01N 59/08* (2013.01)

(58) Field of Classification Search
CPC ........ A01N 43/38; A01N 59/00; A01N 51/00; A01N 47/28; A01N 55/02
See application file for complete search history.

(56) References Cited

U.S. PATENT DOCUMENTS

| 3,036,908 | A | 5/1962 | Günther |
| 5,670,454 | A | 9/1997 | Grossmann et al. |
| 6,372,690 | B1 | 4/2002 | Grégoire et al. |
| 6,972,273 | B2 * | 12/2005 | Sedun ................... A01N 37/32 504/113 |
| 8,076,267 | B2 | 12/2011 | Diebold et al. |
| 8,987,171 | B2 | 3/2015 | Samarajeewa et al. |
| 9,078,401 | B2 * | 7/2015 | Carroll .................... A01G 1/00 |
| 2003/0083202 | A1 * | 5/2003 | Katayama .............. A01N 43/38 504/284 |
| 2009/0028796 | A1 * | 1/2009 | Bednarek ............... A01N 43/38 424/9.2 |
| 2010/0210002 | A1 * | 8/2010 | McCaffrey ............. A01G 33/00 435/257.1 |
| 2011/0306495 | A1 | 12/2011 | Samarajeewa et al. |
| 2014/0349847 | A1 | 11/2014 | Schrader |

FOREIGN PATENT DOCUMENTS

| EP | 1997376 | 3/2008 |
| WO | 9303614 | 3/1993 |
| WO | 2004023876 | 3/2004 |
| WO | 2012032139 | 3/2012 |
| WO | 2012126094 | 9/2012 |
| WO | 2012163824 | 12/2012 |
| WO | 2013078546 | 6/2013 |
| WO | 2013139753 | 9/2013 |
| WO | 2014139012 | 9/2014 |

OTHER PUBLICATIONS

Jensen et al., "Catabolism of Indole-3-Acetic Acid and 4- and 5-Chloroindole-3-Acetic Acid in Bradyrhizobium iaponicum", Journal of Bacteriology, vol. 177, No. 20, Oct. 1995, p. 5762-5766.
Reemer et al., "Auxin and its Role in Plant Development, Chapter 5—Intercellular Transport of Auxin", Springer, pp. 75-100, 2014. (The year of the publication is sufficiently earlier than the effective U.S. filing date so that the particular month of publication is not an issue).
English Abstract of CN103621505(A), "Application of halogenated indole-3-acetic acid as herbicide", published on Mar. 12, 2014.
Kjeld C. Engvild, "Herbicidal activity of 4-chloroindoleacetic acid and other auxing on pea, barley and mustard", Physiologia Plantarum 96: 333-337, 1996.
From Wikipedia, the free encyclopedia, "Auxin", https://en.wikipedia.org/wiki/Auxin, retrieved online on Mar. 17, 2017.
Du RJ et al., "How phytohormone IAA and chelator EDTA affect lead uptake by Zn/Cd hyperaccumulator Picris divaricata", Int J Phytoremediation, Nov.-Dec. 2011; 13(10): 1024-36.
Heath et al., "Chelating Agents and Auxin", No. 4919, vol. 201, Feb. 8, 1964, Nature, pp. 585-587.
Tomaszewski et al., "Interactions of Phenolic Acids, Metallic Ions and Chelating Agents on Auxin-Induced Growth", Plant Physiology Nov. 1966 vol. 41 No. 9 1443-1454.

(Continued)

*Primary Examiner* — Johann R Richter
*Assistant Examiner* — Danielle Sullivan
(74) *Attorney, Agent, or Firm* — Bereskin & Parr LLP/S.E.N.C.R.L., s.r.l.

(57) ABSTRACT

The present application relates to compositions comprising 4-chloroindole-3-acetic acid (4Cl-IAA) or an analogue thereof, or a combination of the latter, in acid, salt or ester form. For example, such compositions can be used to curb weeds.

27 Claims, 17 Drawing Sheets

(56) References Cited

OTHER PUBLICATIONS

Zhou JM et al., "Enhanced phytoextraction of heavy metal contaminated soil by chelating agents and auxin indole-3-acetic acid", Huan Jing Ke Xue, Sep. 2007;28(9):2085-8.
Endmemo, [online], [retrieved on Dec. 4, 2017].Retrieved from the Internet URL:http//www.endmemo.com/sconvert/g_Ippm.php.
Unit Converter, [online], [retrieved on Dec. 4, 2017].Retrieved from the Internet <https://www.translatorscafe.com/unit-converter/en/concentration-solution/2-4/gram%2Fliter-part%2Fmillion/.

* cited by examiner

|  | Trial 1 | Trial 2 | Trial 3 |
|---|---|---|---|
| IA* dose (g/plant) | 0.028 | 0.028 | 0.028 |
| IA concentration (g/L) | 6 | 6 | 6 |
| IA volume (mL/plant) | 4.8 to 7.2 | 3.6 to 4.8 | 3.6 to 6 |
| Number of plants | 20 | 20 | 20 |
| Province | Alberta | Ontario | Québec |
| Hardiness zone | 3B | 5B | 4A |
| Year | 2013 | 2013 | 2013 |
| Period | July to September | June to August | July to September |
| Mean daily temperature per month | 13 to 15 | 17 to 18 | 14 to 21 |
| Cumulative pluviometry (mm) | 84 | 246 | 388 |
| Type of turf | Kentucky bluegrass and fescue | Kentucky bluegrass and fescue | Mixture of various grasses |
| Type of terrain | Experimental station | Experimental station | Experimental station |
| Terrain maintenance | Average | Average | Good |
| Dandelion rating after 7 days | 2.4 | 2.6 | 3.1 |
| Dandelion rating after 40 days | 5 | 4.1 | 4.3 |
| Turf rating after 7 days | 0 | 0 | 1.4 |
| Turf rating after 40 days | 0 | 0 | 0.75 |

FIG. 1A

|  | Trial 4 | Trial 5 | Trial 6 |
|---|---|---|---|
| IA* dose (g/plant) | 0.032 | 0.032 | 0.032 |
| IA concentration (g/L) | 6 | 4.5 | 4.5 |
| IA volume (mL/plant) | 4.8 to 6 | 7.2 | 4.8 to 7.2 |
| Number of plants | 20 | 3 | 20 |
| Province | Québec | Québec | Alberta |
| Hardiness zone | 4A | 4A | 3B |
| Year | 2013 | 2012 | 2012 |
| Period | September | September to October | August to September |
| Mean daily temperature per month | 12 | 7 to 13 | 4 to 8 |
| Cumulative pluviometry (mm) | 58 | 145 | 12 |
| Type of turf | Nonexistent | Mixture of various grasses | Kentucky bluegrass and fescue |
| Type of terrain | Vacant lot | Commercial land | Experimental station |
| Terrain maintenance | None | Poor | Average |
| Dandelion rating after 7 days | 3.3 | 3 | 1.5 |
| Dandelion rating after 40 days | 4.4 | 4.5 | 4.7 |
| Turf rating after 7 days | N/A | 0.7 | 0 |
| Turf rating after 40 days | N/A | 0 | 0 |

FIG. 1B

USE OF 4-CHLOROINDOLE-3-ACETIC ACID FOR CONTROLLING UNWANTED PLANTS

CROSS-REFERENCE TO RELATED APPLICATIONS

The present application is a 35 USC 371 national stage entry of PCT/CA2015/050894 filed on Sep. 15, 2015 and which claims priority on CA 2,863,477 filed on Sep. 16, 2014. These documents are hereby incorporated by reference in their entirety.

FIELD OF THE INVENTION

The invention relates to the field of a selective herbicide for controlling or eliminating weeds while having little or no impact on desirable plants.

BACKGROUND OF THE INVENTION

Synthetic auxinic herbicides were developed around sixty years ago and contributed greatly to changes in agricultural and horticultural practices. These synthetic molecules, copied from the endogenous, or natural, auxins found in plants, are able to control or eliminate several weeds, primarily large-leaved dicotyledonous weeds, generally without overly affecting monocotyledonous plants, primarily grasses. Today, this type of herbicide is used in a wide variety of crops, and even on unfarmed land. Currently, synthetic auxinic herbicides play a major role in managing weeds, whether used alone or with other herbicides or products. Their low production cost and the wide selectivity spectrum developed over the years explain their great success. Indeed, synthetic auxinic herbicides are divided into four classes based on their chemical structure. These four classes, distributed into various sub-classes incorporating several different products, allow a selective control of various species of dicotyledonous weeds found in the agriculture sector as well as the nonprofessional horticulture sector, such as turf management.

The action mode of synthetic auxinic herbicides for sensitive plant species is characterized by an uncontrolled growth often described as an "auxin overdose." The applied dosage causes a variety of metabolic anomalies or disruptions, evolving over time until in most cases, the plant dies. Despite their broad usage spectrum over the years, the exact action mechanism is not fully known, given the cascade of reactions that affect different biochemical pathways in the plant.

2,4-D, or 2,4-dichlorophenoxyacetic acid, is one of the most commonly used synthetic auxinic herbicides. Indeed, it is found in the formulation of several hundred commercially available products, in particular those sold for weed control in turf. Over the last two decades, several studies have shown environmental and human health risks resulting from the use of certain synthetic auxinic herbicides, in particular 2,4-D. Faced with this situation, several countries and territories have decided to ban the use of 2,4-D for lawn maintenance, for example, given the closeness of homes and the purely aesthetic considerations of this practice. In the regions where synthetic auxinic herbicides are prohibited, or in regions without regulations but where users are aware of the issue, various alternative solutions have been developed or studied. However, it appears that to date, these solutions have found only limited success.

The development of a new low-risk selective herbicide for agriculture and horticulture is faced with several challenges, often of competing natures, which makes the approach much more complex. On the one hand, the active ingredient used must be stable enough to withstand various storage and application conditions, but easy enough to break down after application to prevent it from building up in the environment. On the other hand, the active ingredient must lead to quick and obvious symptoms able to comfort the user, in particular for the amateur horticulture sector, but without endangering the desired long-term effect. In other words, the above ground part of the plant must be clearly affected, but without harming the progression of the molecule or product toward the roots in order to ensure permanent elimination of the targeted plant. Lastly, the active ingredient must irreversibly affect the metabolism of the harmful plants or weeds without altering, or excessively disrupting, the growth of the farmed, beneficial or desirable plants. Indeed, the efficacy of a selective herbicide is based on two main parameters, namely the control of the weed to be eliminated and the selectivity of the effect with respect to the desirable plants. These two parameters are influenced by various factors related to the plant itself, the outside environment and the nature of the active ingredient.

In connection with the plant, these factors in particular include:
  how the plant or leaves are carried (spread versus upright),
  the width and shape of the leaves,
  the position or exposure of the meristem,
  the thickness of the cuticle of the leaves,
  the density of the trichomes on the leaves,
  the age of the plant,
  etc.

In terms of the prevailing environment, these factors in particular include:
  the climate conditions,
  the period of the growing season,
  the time of day,
  the type of application (targeted versus spreading),
  etc.

In terms of the nature of the active ingredient, it is in particular necessary to consider:
  the movement or transport pathways of the substance in the plant,
  the interaction with the protein receptors of the plant,
  the mechanisms involved in the action of the substance,
  the type of physiological disruptions caused,
  etc.

There is no solution with a low environmental risk that has been made commercially available in recent years that meets all of the desired criteria. Several alternatives are described here as examples, for the lawn care sector. Acetic acid may kill several species of weeds, but the product is not selective enough. The concentration of acetic acid used to eliminate dicotyledonous plants with wide and spread leaves, such as dandelion, also affects grasses with narrow, upright leaves such as turf. This type of product can therefore be sold only as a nonselective herbicide. The use of an aqueous solution containing from 8 to 20% sodium chloride is also recommended (U.S. Pat. No. 6,372,690 B1), but it appears that this type of product may be difficult to use for spreading-type applications. Furthermore, even in a targeted-type application mode, the product may cause the turf to yellow and have a significant regrowth rate under certain climate conditions. Other products are based on the use of metals such as iron, in chelate form in solution (U.S. Pat. No. 6,972,273 B2). To go beyond the surface or visible necrosis effect alone, several applications are systematically needed.

Such a situation is incompatible with targeted applications. To overcome this difficulty, another invention combines a low concentration of synthetic auxinic herbicide, of the 2,4-D type, with a metal in chelate form (U.S. Pat No. 8,076,267 B2). Although this strategy represents a certain environmental gain, it does not allow access to the growing number of territories where synthetic auxinic herbicides are banned. Furthermore, it should be noted that the chelating agents most commonly used in this type of commercial product, i.e., ethylenediaminetetraacetic acid (EDTA) and hydroxyethylenediaminetriacetic acid (HEDTA), are also implicated in some studies, given their potential buildup in the soil. Work has also been done to use an overdose of indole acetic acid (IAA), a natural plant auxin, to develop a selective herbicide. This endogenous auxin has demonstrated a selective herbicide-type effect, but it is short lasting. The molecule is metabolized quickly by the plant and/or its bond with the protein receptors causes an excessively weak action. Other works have proposed the use of herbicides with a base of synthetic or natural auxins, like IAA, for genetically modified plants after introducing one or several specific genes blocking ethylene synthesis (U.S. Pat. No. 5,670,454). This type of selective herbicide is of limited usefulness, since it is applicable only to certain genetically modified plants. Lastly, it should be noted that in the territories where synthetic auxinic herbicides are prohibited, various decoctions or products of plant origin have a limited effect, such as beet juice and corn gluten. These partial solutions have an effect, following a buildup on the surface or in the soil, on the germination of weed seeds in a pre-established turf.

Work has also been done with another endogenous or natural auxin, having a higher "auxinic" physiological action than IAA, that is found only in a few plant families, namely 4-chloroindole-3-acetic acid (4Cl-IAA). This molecule has for example been found in peas at a given stage of the plant's development. However, Engvild ("Herbicidal activity of 4-indole acetic acid and other auxins on pea, barley and mustard," Physiol. Plant. 96:333-337, 1996) observed in the laboratory that 4Cl-IAA, dissolved in an aqueous solution containing 10% ethanol, had an impact about 4 times lower on the growth of dicotyledonous plants (peas and mustard) compared to 2,4-D. Conversely, the sensitivity of the studied monocotyledonous plant (barley) to 4Cl-IAA was three times higher, still compared with 2,4-D. Indeed, a quantity of 0.17 $g/m^2$ of 4Cl-IAA was sufficient to affect the growth of the monocotyledonous plant (barley) by 50%, versus 0.5 $g/m^2$ with 2,4-D. Similar trends were observed in terms of mortality, expressed in lethal dose for 50% of the plants ($LD_{50}$). Furthermore, the study showed that from one dicotyledonous plant to the other (peas versus mustard), the actual quantities varied greatly, namely by a factor 5. All of these results brought to light a certain capacity to affect vegetation, but appear incompatible with the development of a selective herbicide able to replace 2,4-D. Lastly, a Chinese patent application (CN 103621505 A) was filed on halogenation, in different positions of the carbon cycle, of an IAA molecule for use as an herbicide having concentrations varying from 5 to 90% on a weight basis or 50 to 900 g/L. Considering the low aqueous solubility of this type of molecule (pKa of about 4), an herbicide containing the concentrations recommended in the patent application involves the use of a high organic solvent content that may affect more sensitive grasses and reduce the selectivity of the product accordingly. Furthermore, it should be stressed that a product involving such high concentrations may cause spreading difficulties depending on the required doses.

Therefore, as one can see, there is still a need for a low-risk, selective and effective herbicide able to be used for targeted and/or spreading applications in the professional or amateur horticulture sector and in agriculture.

BRIEF DESCRIPTION OF THE INVENTION

The present invention relates to the use of 4Cl-IAA or an analogue thereof, or a combination of the latter, in acid, salt or ester form for selective weed control.

According to another aspect, the invention relates to a composition comprising 4Cl-IAA, an analogue thereof, or a combination of the latter, in acid, salt or ester form; and a surfactant, a chelating agent, a preservative, a buffer or a combination of the latter.

According to another aspect, the invention relates to a composition comprising 4Cl-IAA, an analogue thereof, or a combination of the latter, in acid, salt or ester form, as defined in the present application, and a co-ingredient.

For example, the use is described for a targeted or spreading application.

For example, the use is described for utilization in the form of a more or less viscous liquid.

For example, the use is described for utilization in the form of a powdered or granular solid.

For example, the use is described for a utilization in the form of a powdered or granular solid, optionally obtained from a solution of 4Cl-IAA or an analogue thereof, or a combination of the latter, in acid, salt or ester form, said solution being absorbed or retained on a solid matrix or in the form of a solid obtained from a crystalline form of 4Cl-IAA mixed with other more or less active solid inputs.

For example, the 4Cl-IAA, an analogue thereof, or a combination of the latter, in acid, salt or ester form, is present in a concentration varying from 1.5 g/L to 40 g/L.

For example, the 4Cl-IAA, an analogue thereof, or a combination of the latter, in acid, salt or ester form, is present in a concentration varying from 1 g/L to 40 g/L.

For example, the 4Cl-IAA, an analogue thereof, or a combination of the latter, in acid, salt or ester form, is present in a concentration varying from 2 g/L to 10 g/L.

The present invention relates to a composition comprising 4Cl-IAA, an analogue thereof, or a combination of the latter, in acid, salt or ester form, as defined according to the invention, and a co-ingredient.

For example, the co-ingredient causes visible and rapid damage to the foliage and/or stem and/or flower.

For example, the co-ingredient causes an overdose of nutrients and/or metal toxicity and/or osmotic shock and/or any other visible metabolic disruption.

For example, the co-ingredient is a chelated or non-chelated metal, at a concentration varying from 0.1 to 5% on a weight basis.

For example, the co-ingredient is sodium chloride, at a concentration varying from 1 to 36% on a weight basis.

For example, the co-ingredient is urea, at a concentration varying from 1 to 50% on a weight basis.

For example, the co-ingredient is a fatty acid, at a concentration varying from 1 to 20% on a weight basis.

The invention describes the use of the composition according to the invention for selective weed control.

The invention describes the use of the composition for a targeted or spreading application.

The invention describes the use of the composition for an application in the form of a more or less viscous liquid.

For example, the composition is in the form of a powdered or granular solid.

For example, the composition is in the form of a powdered or granular solid, optionally obtained from a solution of 4Cl-IAA or an analogue thereof, or a combination of the latter, in acid, salt or ester form, said solution being absorbed or retained on a solid matrix or in the form of a solid obtained from a crystalline form of 4Cl-IAA mixed with other more or less active solid inputs.

For example, the 4Cl-IAA, an analogue thereof, or a combination of the latter, is present, in acid or salt form, in a concentration varying from 1 g/L to 40 g/L.

For example, the 4Cl-IAA, an analogue thereof, or a combination of the latter, is present, in acid or salt form, in a concentration varying from 1.5 g/L to 40 g/L.

For example, the 4Cl-IAA, an analogue thereof, or a combination of the latter, is present, in acid or salt form, in a concentration varying from 2 g/L to 10 g/L.

For example, the 4Cl-IAA, an analogue thereof, or a combination of the latter is used at a dose greater than or equal to 0.01 g/plant and less than or equal to 0.1 g/plant for a targeted application.

For example, the 4Cl-IAA, or an analogue thereof, or a combination of the latter, in acid, salt or ester form, is used at a dose greater than or equal to 0.005 g/plant and less than or equal to 0.1 g/plant for a targeted application.

For example, the 4Cl-IAA, an analogue thereof or a combination of the latter, in acid, salt or ester form, is used at a dose greater than or equal to 0.01 g/plant and less than or equal to 0.05 g/plant for a targeted application.

For example, the 4Cl-IAA, an analogue thereof, or a combination of the latter is used at a dose greater than or equal to 0.1 g/m$^2$ and less than or equal to 1.0 g/m$^2$ for a spreading application.

For example, the 4Cl-IAA, an analogue thereof or a combination of the latter, in acid, salt or ester form, is used at a dose greater than or equal to 0.05 g/m$^2$ and less than or equal to 1.0 g/m$^2$ for a spreading application.

For example, the 4Cl-IAA, an analogue thereof or a combination of the latter, in acid, salt or ester form, is used at a dose greater than or equal to 0.2 g/m$^2$ and less than or equal to 0.8 g/m$^2$ for a spreading application.

For example, the usage of the invention is done in one or several applications at similar or different doses.

For example, the targeted dose during usage of the invention is obtained after one or several applications.

For example, the invention is used once or repeatedly.

For example, the use of the 4Cl-IAA molecule or an analogue thereof, or a combination of the latter, in acid, salt or ester form, is combined with a surfactant, a chelating agent, a preservative, a buffer or a combination of the latter.

For example, the chelating agent can be chosen from cyclohexanediaminetetraacetic acid (CDTA), ethylenediamine-N,N'-disuccinic acid (EDDS), EDTA, ethanol diglycine (EDG), HEDTA, methylglycinediacetic acid, glutamicadiacetic acid, trans-1,2-diaminocyclohexane-N,N,N', N'tetraacetic acid, diethylenetriaminepentaacetic acid (DTPA), iminodisuccinic acid, the salts thereof (e.g., the sodium and potassium salts), and combinations thereof.

For example, the chelating agent may be chosen from HEDTA, EDTA, DTPA, EDDS, the salts thereof, and combinations thereof.

For example, the chelating agent is present at a concentration from about 0.05% to about 5% on a weight basis.

For example, the chelating agent is present at a concentration from about 0.1% to about 3% on a weight basis.

For example, the surfactant may be chosen from an anionic surfactant (for example, sulfate, sulfonate, phosphate or carboxylate alkyl); cationic surfactant (for example, amines or quaternary ammoniums); zwitterionic surfactants (for example, phosphatidylcholine); or non-ionic surfactants (for example, glycol, alcohol, glucoside, glycerol alkyls, as well as polysorbates and Spans).

For example, the 4Cl-IAA, or an analogue thereof, or a combination of the latter, in acid, salt or ester form, is used in the form of a potassium salt, a sodium salt or an amine salt.

DEFINITIONS

Low-risk herbicide: herbicide having zero or low inherent toxicity qualities for health and the environment.

Analogue of 4Cl-IAA: molecule having a chemical structure similar to 4Cl-IAA, but differing therefrom by the position of the chlorine on the aromatic cycle.

The term 4Cl-IAA, when used in the application, may include an analogue thereof, or a combination of the latter, in acid, salt or ester form.

Weeds: unwanted or adventitious plants that one wishes to eliminate for various reasons, often part of cotyledons groups that may have varied foliage morphologies, in particular wide leaves, like dandelion and plantain. Table 1 lists some weeds as an example.

TABLE 1

Non-exhaustive list of weeds.

| Latin name | Common name |
| --- | --- |
| Arctium lappa | Burdock |
| Circium arvense | Thistle |
| Hieracium pilosella | Hawkweed |
| Leontodon autumnalis | Autumn hawkbit |
| Medicago lupulina | Lupulin |
| Taraxacum officinale | Dandelion |
| Plantago sp. | Plantain |
| Potentilla reptans | Potentilla |
| Trifolium repens | Clover |
| Tussilago farfara | Coltsfoot |

Desirable plants: plants whose reproduction and growth are favored for aesthetic and/or economic reasons, often monocotyledonous, in particular grasses such as turf and wheat.

Control: eradication of weeds assessed, after a certain length of time, based on a visible damage rating of the foliage, varying from 0 to 5, and/or the mortality percentage observed on the treated plants.

TABLE 2

Assessment of the ability to control weeds.

| Value | Qualification of the effect* | Description | User perception |
|---|---|---|---|
| Damage rating of the weed | | | |
| 0 to 0.9 | Absence | No leaves are affected | Unacceptable |
| 1 to 1.9 | Very slight | Effect on the foliage barely perceptible | |
| 2 to 2.9 | Slight | Some leaves are clearly affected | |
| 3 to 3.9 | Strong | Majority of the leaves are affected, causing loss of chlorophyllous functions | Acceptable |
| 4 to 4.9 | Very strong | All of the leaves are greatly affected | Ideal |
| 5 | Death or appearance of mortality | All of the visible parts of the plant are dead | |
| Weed mortality percentage | | | |
| 0 to 100 | % of dead plants relative to total number of plants treated | All of the tissues are affected, including those of the roots, such that the plant is already dead or about to die. | Preferably 60% and above Ideally 80% and above |

*Effect: necrosis and/or deformation and/or drying

Selectivity of the effect: absence of a pronounced effect of the herbicide on the desirable plants assessed based on an impact rating on the latter, varying from 0 to 3 in the case of turf.

TABLE 3

Assessment of the selectivity of an herbicide by the turf impact rating

| Value | Qualification of the effect* | Description | User perception |
|---|---|---|---|
| 0 to 0.9 | Absence | No leaves are affected or slight yellowing difficult to discern | Ideal |
| 1 to 2 | Average | Discernible yellowing | Acceptable |
| 2.1 to 3 | Strong | Very pronounced yellowing | Unacceptable |

*Effect: yellowing and/or drying

Targeted application: application of the product on a given plant using a device making it possible to spray a predetermined volume of fluid in a defined zone in order to reduce the quantity of product to be used and the potential effect on the surrounding plants, in particular in amateur horticulture.

Spreading application: application of a product on a given surface area of land covered with plants using a device spraying a volume of liquid at a predetermined flow rate and where the device can be moved at a constant speed to cover a larger surface, in particular in agriculture and professional horticulture.

Dose: quantity of product, such as 4Cl-IAA or an analogue thereof, or a combination of the latter, in acid, salt or ester form, used during an application.

BRIEF DESCRIPTION OF THE DRAWINGS

FIG. 1 Efficacy of 4Cl-IAA on dandelion damage and the impact rating on turf assessed for targeted applications under various conditions.

DETAILED DESCRIPTION OF THE INVENTION

Figure 2:
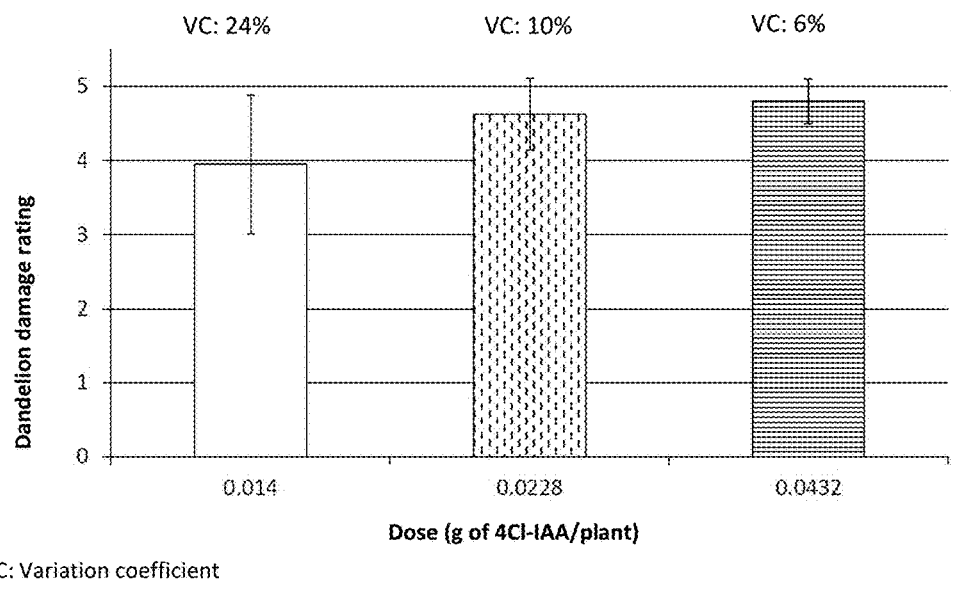
FIG. 2 Effect of the dose of 4Cl-IAA on dandelion damage assessed for targeted applications.

The present invention consists of a solution of 4Cl-IAA, or an analogue thereof, or a combination of the latter, in acid, salt or ester form, able to selectively eliminate several types of weeds encountered in horticulture and/or agriculture in different situations or conditions. This solution can be used in the form of a more or less viscous liquid. Alternatively, this solution can be absorbed or retained on a solid matrix for use in the form of a powdered or granular solid. In one embodiment, the solution is obtained from water and a potassium salt, a sodium salt or an amine salt such as triethanolamine, ethylenediamine or oligoamines. In another embodiment, the crystalline form of the 4Cl-IAA or an analogue thereof, a combination of the latter, in acid, salt or ester form, can be mixed with other, more or less active solid inputs, to be used in a powdered or granular form 4Cl-IAA is a natural molecule that shows little or no toxicity for health and the environment, preventing it from being banned from use.

It has been observed that doses of 0.01 to 0.1 g/plant per application, used in a targeted manner on the foliage, were causing gradual blight able to spread over several weeks depending on the growing season, type of weed, age of the plant and climate conditions. Typically, the physiological disruptions caused by the invention are manifested by a more or less pronounced epinasty, wilting and/or curvature of the leaves and/or stem and/or flowers after several hours, blockage of growth after 24 hours, and the appearance of more or less obvious reddish spots and/or chloroses after 3 to 5 days. Preferably, the doses to be applied are between 0.02 and 0.08 g/plant, and ideally between 0.03 and 0.06 g/plant. It is interesting to emphasize that a 4Cl-IAA solution ultimately has control capacities of the same magnitude as those observed with a 2,4-D-based synthetic auxinic herbicide. Using the hypothesis that a dandelion, for example, occupies a surface of 100 $cm^2$, corresponding to a more or less square zone of 10 cm×10 cm, there would be 100 dandelions on a surface of 1 $m^2$. If each dandelion receives a dose of 0.01 g, for instance, 1 g is applied over the zone of 1 $m^2$ completely covered with dandelions. It is thus possible to express the doses previously presented in grams per square meter instead in grams per plant.

Following this conversion, the corresponding doses are therefore from 1 to 10 $g/m^2$ for targeted applications over a surface completely covered with dandelions.

The efficacy of a selective herbicide is based on two main parameters, namely the ability to control weeds combined with the minimum applicable dose and the selectivity of the effect with respect to the desirable plants. This last parameter makes it possible to determine the maximum applicable dose. At doses below 0.01 g/plant, one observes low control capacities and/or excessive variability surrounding this capacity. It should be noted that the control capacity is expressed in the form of a damage rating of the foliage ranging from 1 to 5 and/or a mortality percentage of the targeted plant. The damage rating is useful to assess the user's perception of the efficacy of the product, since it is assigned based on the appearance of the external foliage. The mortality percentage in turn provides information on the ultimate efficacy of the product, since it is computed from the number of plants that have actually died or disappeared after a given length of time. The approval agencies use this last assessment method greatly. As an example, a product allowing a weed mortality rate of 80% will, in some jurisdictions, bear the word “eliminates” on its label, while a product with a rate of 60% will be described as “suppressing.” These nuances may have a significant impact on informed users' choice of herbicide.

For spreading applications, the doses are between 0.1 $g/m^2$ and 1.0 $g/m^2$ per application. Preferably, the doses to be applied are between 0.3 and 0.8 $g/m^2$, and ideally between 0.4 and 0.6 $g/m^2$. These doses are smaller than the doses determined for targeted applications, which would vary from 1 $g/m^2$ to 10 $g/m^2$ if the considered zone was completely covered with dandelions, i.e., 100 dandelions receiving 0.01 and 0.1 g/plant. This smaller quantity of 4Cl-IAA used must be analyzed based on the two parameters selected to describe the efficacy of a selective herbicide, i.e., the control capacity and the selectivity of the effect with respect to the desirable plants. Indeed, the reduced quantity is related to the selectivity aspect, or effect on the turf as an example. With a spreading application, the product is distributed uniformly over the entire treated surface.

The turf receives as much product as the weeds, unlike a targeted application, where the majority of the product reaches the weeds. Indeed, with a targeted application, the quantity of product touching the turf most often originates from a drift phenomenon. If the desirable plants, for example the turf, receive the same dose as the weeds, this dose must be reduced to eliminate or minimize the perceived impact on these desirable plants. This decrease in the dose will of course have certain consequences on the weed control capacity, in particular resulting in a slower appearance of visible damage. In the context of a spreading application, this shift may be tolerated, since the user, most often a professional, is in a different perception dynamic from that prevailing in a targeted application context. In the latter case, the user is most often a consumer anxious to see the weed that is inconveniencing him disappear. It is also important to mention that when yellowing of the turf is observable, it decreases and disappears entirely with time, unlike the weed, which move inexorably toward their death, showing the selectivity of the molecule at the established doses. In the case of large-leaved weeds present in the turf, this selectivity will therefore be based not only on morphological differences (carriage of the plant and position of the meristem) responsible for a differential absorption, but also in all likelihood on different metabolic reactions.

Furthermore, it has been observed that the different identified doses must be applied with a solution having concentrations greater than or equal to 1.5 g/L and lower than 40 g/L. Solutions having concentrations below 1.5 g/L create an excessively weak propelling force or excessively low concentration gradient on the surface of the leaf. Such a situation slows the penetration of the product in the leaf, and possibly its subsequent movement in the plant, which results in a lower control capacity that may appear less attractive to some users. At the other extreme, a solution having a concentration above 40 g/L implies application volumes reduced too much by the established doses. As an example, it would be necessary to apply 12.5 mL of product with a concentration of 40 g/L on one square meter for a spreading dose of 0.5 $g/m^2$, which proves difficult in light of the existing equipment. For a targeted application with a dose of 0.05 g/plant, it would be necessary to use only 1.25 mL on a plant having, by way of illustration, a surface of 100 $cm^2$, which also proves difficult for an adequate application.

It should also be noted relative to the invention that the dose of product can be applied just once on a given zone, or can be subject to several applications, for both considered types of application. Such flexibility is of interest when dealing with certain weeds that are more troublesome due to their size, for example. In the same vein as discussed above, it may be advisable, as an example, to perform several spreading applications, more or less spaced apart, when the season is drier or further along and the turf is more sensitive. As an illustration, the dose per application used can be in the lower part of the recommended range under such conditions.

It is important to stress that 4Cl-IAA, like other endogenous auxins, is a molecule that moves primarily in the plant by polar transport. This mode of transport is much slower than the nonpolar transport observed with other substances moving in the xylem and the phloem. A rate of 5 to 20 cm/h is discussed for nonpolar transport, compared to a movement of 5 to 20 mm/h for polar transport. In the latter case, the movement is done slowly, but inexorably, from cell to cell, going from the stem to the root. According to the literature (Reemmer and Murphy, 2014, *Auxin and its Role in Plant Development,* Springer edition, pages 75 to 100), synthetic auxins such as 2,4-D and naphtalene-1-acetic acid (NAA) move more quickly in the plant than IAA and 4Cl-IAA. This situation therefore explains the slower observed response regarding weed control with one of the embodiments of the present invention relative to a synthetic auxinic herbicide, even if, ultimately, the result is comparable. In the case of a product for targeted application against dandelions intended for the consumer market, as an example, this shift in the response may represent a drawback relative to a faster synthetic or conventional auxinic herbicide. To overcome this difficulty, one preferred embodiment of the present invention incorporates a co-ingredient moving less slowly, by nonpolar transport for example, and able to cause quick surface necrosis or more or less permanent visible damage to the foliage and/or the stem. Several action strategies can be used to this end: damage associated with a nutrient overdose, osmotic shock, toxicity related to a chelated or non-chelated metal, and/or any other visible metabolic disruption occurring quickly, for example with another auxin that may be synthetic (for example. 2,4-dichlorophenoxyacetic acid (2,4-D) or 3,6-dichloro-2-methoxybenzoic acid (Dicamba)) or natural (for example, indole-3-acetic acid (IAA), indole-3-butyric acid (IBA), etc). As an example, it is recommended to use concentrations, on a weight basis, from 0.1 to 5% for metals, such as iron and manganese, irrespective of whether they are chelated (HEDTA or EDTA, for example), from 1 to 36% for sodium chloride or manganese chlorate, from 1 to 50%, preferably 5-15%, for urea and from 1 to 20% for fatty acids, such as carboxylic and phosphonic acids. It should be noted that the disruption causing a short-term visible effect does not need to be permanent or fatal for the plant, since the 4Cl-IAA will take over. As an illustration, a solution containing 0.45% of 4Cl-IAA combined with 10% of urea makes it possible to obtain a damage rating of 3.4 after 3 days, whereas a solution of 4Cl-IAA alone shows only a small effect after the same amount of time. It should be noted that after 35 days, both solutions have a maximum rating of 5 for dandelion control. The same phenomenon occurs with spreading applications.

Aside from its efficacy under the described conditions, the invention has other advantages. The 4Cl-IAA molecule can be formulated with various formulation agents in order to better adapt the properties of the finished product to the different encountered application contexts. On the one hand, buffer solutions, preservatives, such as Proxel™, surfactants, such as Tween™, and thickeners can be added alone or in combination, depending on what is needed.

On the other hand, it is possible to use chelating or sequestering agents in order to facilitate penetration of the molecule in the plant. Indeed, it may be desirable to reduce the dose of 4Cl-IAA applied and/or the concentration of this molecule in the finished product in the context, for instance, of a more fragile turf or a given type of weed. The different families of chelating or sequestering agents that may be used are, but are not limited to, carboxylic acids (for example, aminopolycarboxylic acids, aromatic carboxylic acids, aliphatic carboxylic acids), amino acids, hydroxycarboxylic acids, carboxylic ether acids, as well as phosphonic acids. It should be noted that these products can be incorporated into the formulation in acid or salt form.

As an illustration, the addition of hydroxyethylenediaminetriacetic acid (HEDTA) or hydroxy ethylene diamine disuccinic acid (EDDS) made it possible to halve the tested minimum dose without chelating agent for a formulation with or without incorporating a co-ingredient. Indeed, for doses of 0.0075 g per plant, an interesting increase was observed in the damage rating on dandelions (from 3.1 to 4.3), as well as a reduced variability of the observed results expressed in the form of variation coefficient (from 29 to 15%). Likewise, it appears that the chelating agents make it possible to reduce the concentration of 4Cl-IAA in the solution to concentrations as low as 1 g per liter without affecting the desired efficacy. It should also be noted that the product can be sold in concentrated form and diluted upon use or application to comply with the identified doses.

Peroxide deterioration tests demonstrated that 4Cl-IAA offers a certain stability. Indeed, a finished product incorporating the molecule shows stability over two years in storage at room temperature. Interestingly, the literature indicates that the molecule can be catabolized by bacteria from the soil such as *Bradyrhizobium japonicum* via the same metabolic pathways known for IAA (Jensen JB, Egsgaard H, Van Onckelen H, Jochimsen BU, Catabolism of indole-3-acetic acid and 4- and 5-chloroindole-3-acetic acid in *Bradyrhizobium japonicum*, 1995, J. Bacteriol. 177 (20) : 5762-6).

Lastly, the present invention can also be implemented with an analogue related to the position of the chlorine on the aromatic cycle or with one of the esters, natural or not, such as the methyl ester, for example, of the 4Cl-IAA molecule or one of its analogues. A given product based on one of these different molecules or a combination thereof therefore makes it possible to control a multitude of weeds in the professional or nonprofessional horticulture sector and the agriculture sector.

Although the invention is described using certain preferred embodiments, in particular in the examples, these must not limit the scope of the invention. On the contrary, alternatives, modifications and equivalents are considered, as they may be defined by the present application. The objects, advantages, aspects and other features of the invention will become clearer and will be better understood in light of the non-limiting description of the invention, in particular owing to the figures in the application.

EXAMPLES

The following examples show the efficacy of a new selective herbicide based on the use of the 4Cl-IAA molecule according to certain embodiments of the present invention.

Example 1

Title

Efficacy of 4Cl-IAA on dandelion damage and the impact rating on turf assessed for targeted applications under various conditions.

Methodology

The experiments were conducted according to completely randomized design and randomized complete block design with targeted applications for dandelion control on various turfed terrain.

Treatment: 4Cl-IAA without co-ingredient

Dependent variable: mean damage rating (from 0 to 5) on the dandelions and impact rating (from 0 to 3) on the turf assessed after 7 and 40 days.

The results are shown in FIG. 1.

Interpretation

The product showed relatively constant dandelion control efficacy and turf impact despite highly variable weather conditions (mean daily temperature from 4 to 21 degrees Celsius, pluviometry from 12 to 388 mm and hardiness zone from 3B to 5B and season from June to October) and different operators involved in taking data (subjective rating assessment). This is therefore a robust product faced with different usage conditions.

Example 2

Title

Effect of the dose of 4Cl-IAA on dandelion control assessed according to the damage rating for targeted applications.

Methodology

The experiment was conducted using a randomized complete block design. Four repetitions were done for each treatment.

Treatment: 4Cl-IAA without co-ingredient

Dependent variable: mean damage rating (from 0 to 5) with the variation coefficient assessed after 42 days.

The results are shown in FIG. 2.

Interpretation

Damage rating of the weed=control (perceived effect)

At doses below 0.01 g/plant, the damage rating decreases, and above all, the variability surrounding the latter increases considerably, which yields a less reliable product.

Example 3

Title

Effect of the dose of 4Cl-IAA on dandelion control assessed using the mortality percentage for targeted applications.

Methodology

The experiment was conducted using a randomized complete block design. Four repetitions were done for each treatment.

Treatment: 4Cl-IAA without co-ingredient

Dependent variable: Mean mortality percentage with the variation coefficient assessed after 42 days.

Figure 3:
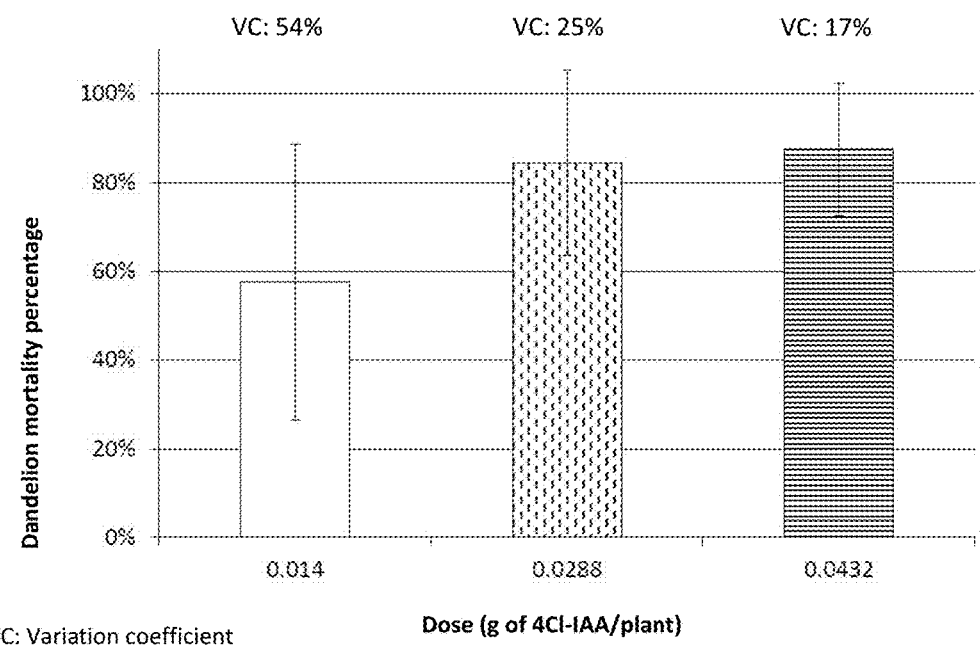
FIG. 3 Effect of the dose of 4Cl-IAA on dandelion mortality for targeted applications.

The results are shown in FIG. 3.

Interpretation

Weed mortality percentage=control (final effect)

At doses below 0.01 g/plant, the mortality percentage decreases by about 50% (below the 60% corresponding to the "suppressed" mention on the label) and the variability surrounding this percentage increases greatly, which yields a relatively unreliable product.

Example 4

Title

Effect of the dose of 4Cl-IAA on the selectivity of the product assessed according to the turf impact rating for targeted applications Methodology The experiment was conducted using a randomized complete block design. Five repetitions were done for each treatment.

Treatment: 4Cl-IAA without co-ingredient

Dependent variable: Impact rating (from 0 to 3) on the turf assessed after 7 days.

Figure 4:
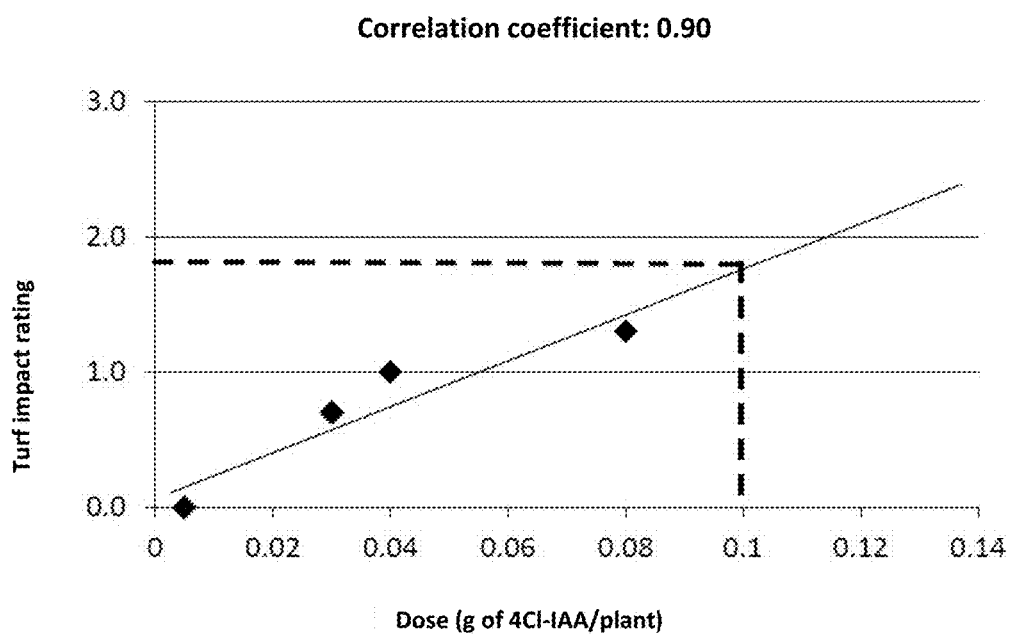
FIG. 4 Effect of the dose of 4Cl-IAA on selectivity regarding with turf for targeted applications.

The results are shown in FIG. 4.

Interpretation

Turf impact rating=selectivity

At doses below 0.1 g/plant, the turf impact goes from zero to acceptable. Beyond a dose of 0.1 g/plant, the turf impact becomes too visible and the risk of exceeding the acceptable rating increases, more or less quickly depending on the prevailing situation, in particular in terms of the condition of the turf.

Example 5

Title

Effect of the dose of 4Cl-IAA on dandelion and burdock control for targeted applications Methodology The experiment was conducted using a randomized complete block design. Five repetitions were done for each treatment.

Treatment: 4Cl-IAA without co-ingredient applied at a dose of 0.015 g/plant with a concentration of 1.9 and 7.5 g/L Dependent variable: mean damage rating (from 0 to 5)

Figure 5A:
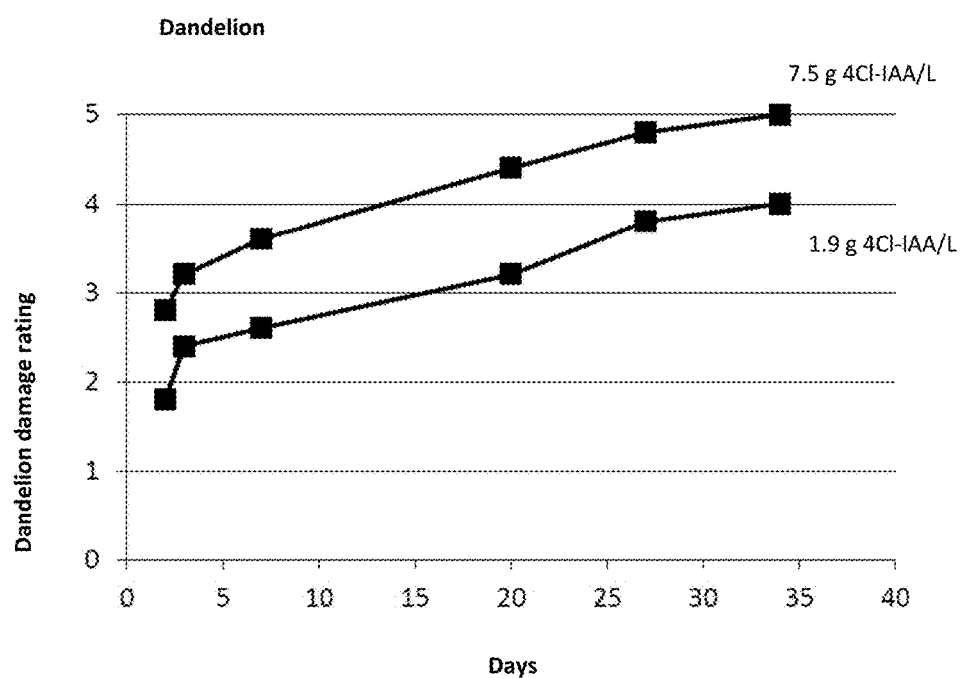
FIG. 5 Effect of the dose of 4Cl-IAA on dandelion (5A) and burdock (5B) for targeted applications.
Figure 5B:
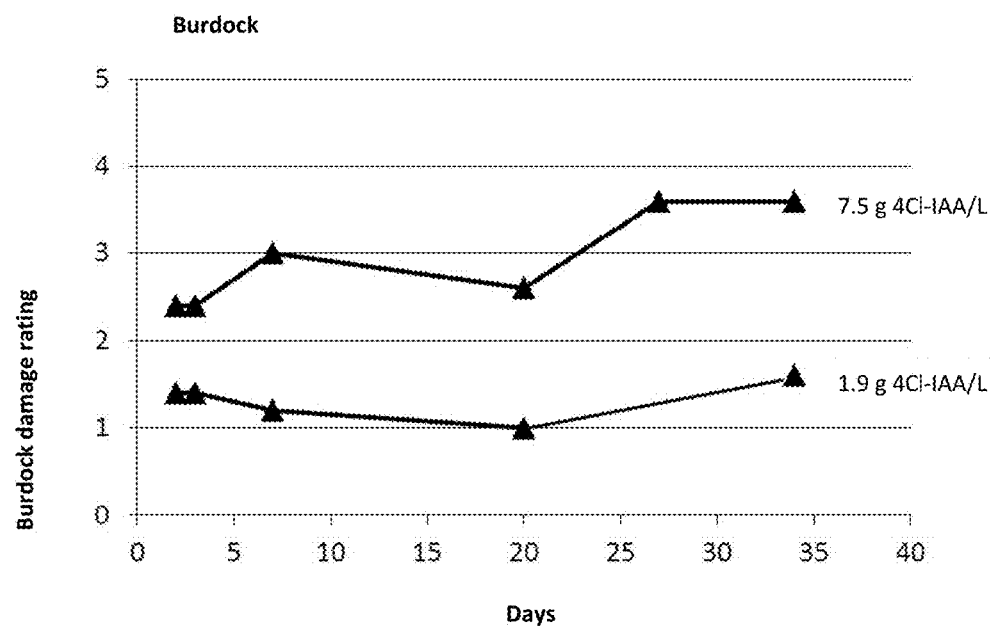

The results are shown in FIG. 5A (dandelion) and FIG. 5B (burdock).

Interpretation

Damage rating of the weed =control (perceived effect)

With concentrations below 1.9 g/L, the weed control efficacy is slowed and/or reduced excessively.

Example 6

Title

Effect of urea as co-ingredient of the 4Cl-IAA on dandelion control for targeted applications Methodology The experiment was conducted using a randomized complete block design. Four repetitions were done for each treatment.

Treatment: solution of 4Cl-IAA applied at a dose of 0.03 g/plant containing 10% urea as co-ingredient Dependent variable: mean damage rating (from 0 to 5)

Figure 6:
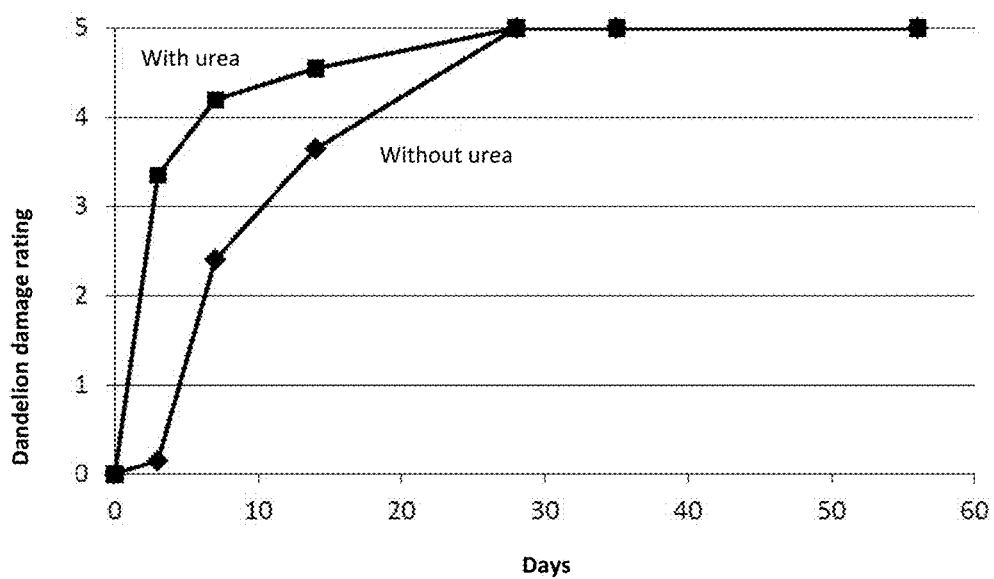
FIG. 6 Effect of urea over time as co-ingredient on dandelion control for targeted applications.

The results are shown in FIG. 6.

Interpretation

Damage rating of the weed=control (perceived effect)

The addition of 10% urea as co-ingredient accelerates the dandelion control efficacy perceived by the user, particularly during the first 72 hours. After 30 days, the two formulations come together in terms of efficacy.

Example 7

Title

Effect of iron, manganese, salt and urea as co-ingredient(s) on dandelion control for targeted applications Methodology The experiment was conducted using a randomized complete block design. Four repetitions were done for each treatment, except for iron chelate, where three repetitions were done.

Figure 7:
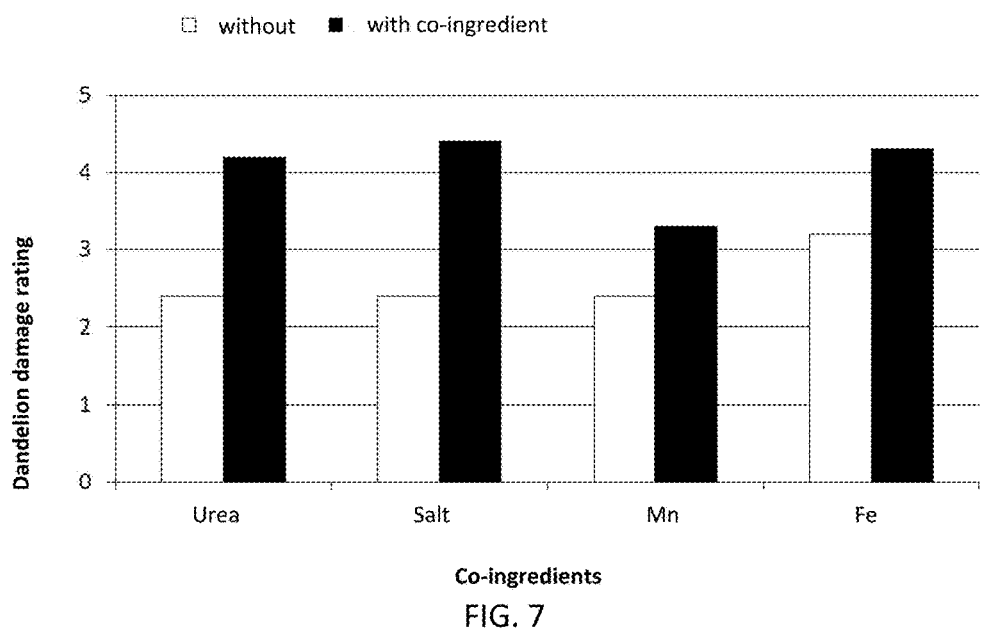
FIG. 7 Comparison of iron, manganese, salt and urea as co-ingredient on dandelion for targeted applications.

Treatment: solutions of 4Cl-IAA applied at doses of 0.02 to 0.03 g/plant containing 10% urea or 6% sodium chloride or 0.24% iron chelate (HEDTA) or 0.1% manganese chelate (HEDTA) as co-ingredient Dependent variable: mean damage rating (from 0 to 5) assessed after 7 days The results are shown in FIG. 7.

Interpretation

Damage rating of the weed=control (perceived effect)

All three types of co-ingredients caused a pronounced acceleration in the control efficacy perceived by the user.

Example 8

Title

Comparison of the effect of 4Cl-IAA with other auxins on dandelion control for targeted applications Methodology The experiment was conducted using a randomized complete block design. Four repetitions were done for each treatment, except for 4Cl-IAA methyl ester, where three repetitions were done.

Treatment: the applied quantities varied from 0.014 to 0.036 g/plant, except for IAA, where the quantity was higher (0.2 g/plant) in light of the information found in the literature on the effect of the latter.

Figure 8:
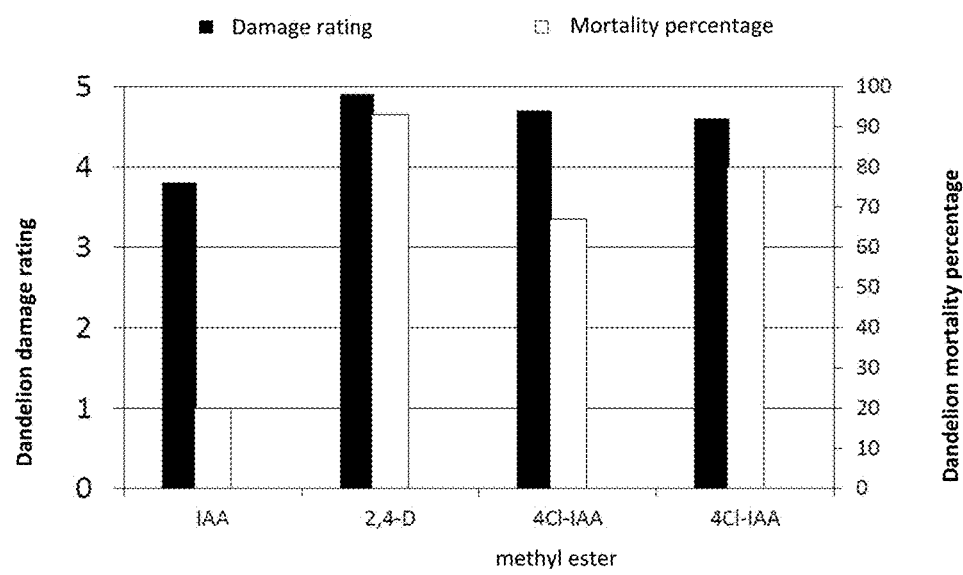
FIG. 8 Comparison of the effect of 4Cl-IAA with other auxins on dandelion for targeted applications.

Dependent variable: mean damage rating (from 0 to 5) and mean mortality percentage assessed between 28 and 35 days after application The results are shown in FIG. 8.

Interpretation

Damage rating of the weed=control (perceived effect)

Weed mortality percentage=control (final effect)

The 4Cl-IAA and its methyl ester show control efficacies close to those observed with a 2,4-D-based herbicide. It is possible that the methyl ester of 4Cl-IAA is converted into 4Cl-IAA in the plant. The use of IAA shows an interesting damage rating, but a low mortality percentage for a higher quantity. This last result indicates a metabolization of the molecule by the plant or a weaker action of the molecule on the plant allowing regrowth of the leaves and/or survival of the plant.

Example 9

Title

Effect of a targeted second application on plantain control for different doses of 4Cl-IAA Methodology The experiment was conducted using randomized complete block design. Four repetitions were done for each treatment.

Figure 9:
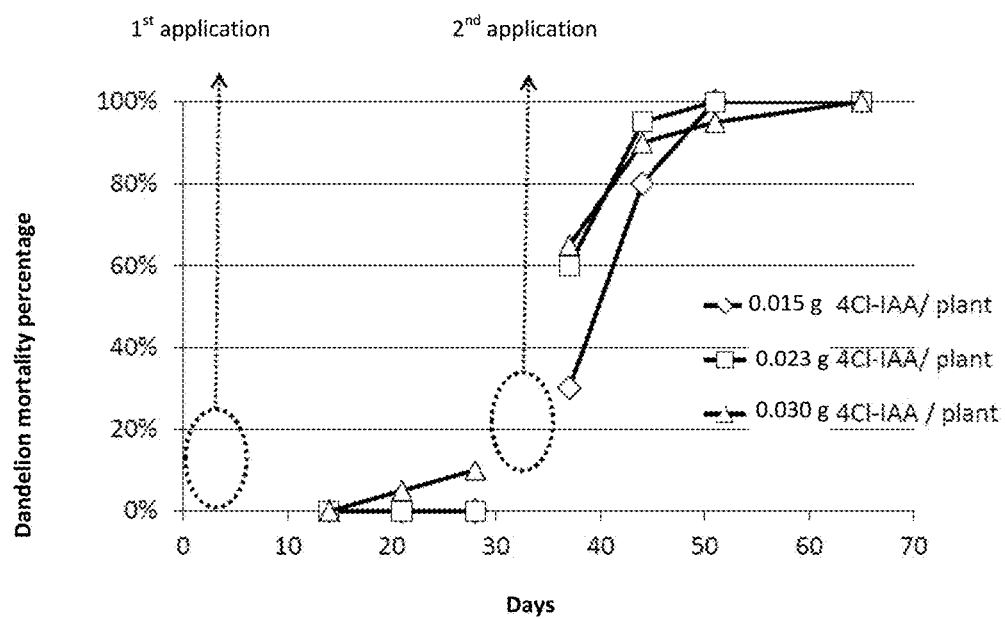
FIG. 9 Effect of a targeted second application on plantain for different doses of 4Cl-IAA.

Treatment: 4 Cl-IAA without co-ingredient at three doses, i.e., 0.015, 0.023 and 0.030 g/plant Dependent variable: mean mortality percentage The results are shown in FIG. 9.

Interpretation

Weed mortality percentage=control (final effect)

Under certain usage conditions, a second application can provide a pronounced improvement in the control efficacy. Furthermore, it appears that two applications of 0.015 g/plant could be more effective than one application of 0.030 g/plant.

Example 10

Title

Weed species studied and able to be controlled with targeted applications of 4Cl-IAA Methodology The experiments were conducted according to completely randomized design and randomized complete block design with targeted applications for weed control on various terrain covered in turf.

Treatment: 4 CL-IAA without co-ingredient with doses varying from 0.022 to 0.036 g/plant Variables: Observation of a damage rating above 4 and a mortality percentage above 80%, assessed after a period of 21 to 40 days, depending on the species.

TABLE 4

Foliar morphology of different dicotyledonous weeds.

| Latin name | Common name | Leaf morphology | | |
|---|---|---|---|---|
| | | Trichome density | Cuticle thickness | Type of foliar limb |
| Arctium lappa | Burdock | Strong | Weak | Whole |
| Circium arvense | Thistle | Weak | Average | Whole |
| Hieracium pilosella | Hawkweed | Strong | Weak | Whole |
| Leontodon autumnalis | Autumn hawkbit | Strong | Average | Whole |
| Medicago lupulina | Lupulin | Strong | Weak | Segmented |
| Taraxacum officinale | Dandelion | Weak | Average | Whole |
| Plantago sp. | Plantain | Weak | Strong | Whole |
| Potentilla reptans | Potentilla | Average | Average | Segmented |
| Trifolium repens | Clover | Strong | Weak | Segmented |
| Tussilago farfara | Coltsfoot | Strong | Average | Whole |

Interpretation

Weed damage rating=control (effect perceived)

Weed mortality percentage=control (final effect)

With doses of the same magnitude, 4Cl-IAA makes it possible to control several dicotyledonous weed species having various foliar morphologies that may influence the absorption of a substance. This is therefore a versatile product working with different weed species.

Example 11

Title

Effect of the dose of 4Cl-IAA on dandelion control and selectivity of the product for spreading applications Methodology The experiment was conducted using a randomized complete block design. Three repetitions were done for each treatment with surface areas of 0.5 m$^2$.

Treatment: 4Cl-IAA without co-ingredient with an application rate of 100 mL/m$^2$ Dependent variable: mean damage rating (from 0 to 5) of the dandelion and mean impact rating (from 0 to 3) on the turf assessed after 50 days

TABLE 5

Effect of the dose of 4Cl-IAA on dandelion control

| Dose (g/m$^2$) | 1.2 | 1.0 | 0.6 | 0.3 |
|---|---|---|---|---|
| Dandelion damage rating | 3.9 | 3.8 | 4.1 | 3.0 |
| Turf impact rating | 2.0 | 1.7 | 1.7 | 0.7 |

Interpretation

Weed damage rating=control (effect perceived)

Turf impact rating=selectivity

A dose of 4Cl-IAA of 1.2 g/m$^2$ and above risks affecting the turf excessively, and a dose of 0.3 g/m$^2$ shows a control efficacy that is still acceptable.

Example 12

Title

Effect over time of the dose on the selectivity of the product and turf regrowth for spreading applications of 4Cl-IAA Methodology The experiment was conducted using a completely randomized design with surface areas of 2 m$^2$ per treatment.

Treatment: 4Cl-IAA without co-ingredient with an application rate of 100 mL/m$^2$ Dependent variable: impact rating (from 0 to 3) on the turf assessed after 4 and 90 days

TABLE 6

Effect at 4 or 90 days of an application of 4Cl-IAA

| Dose (g/m$^2$) | 1.2 | 1.0 | 0.9 | 0.6 | 0.25 |
|---|---|---|---|---|---|
| After 4 days | 3 | 2 | 1 | 1 | 0 |
| After 90 days | 0 | 0 | 0 | 0 | 0 |

Interpretation

Weed damage rating=control (effect perceived)

Even when highly affected, the turf recovers well and becomes green again after 90 days, unlike the weeds, which move inexorably toward their death.

Example 13

Title

Effect of urea as co-ingredient of the 4Cl-IAA on dandelion control for spreading applications at different doses Methodology The experiment was conducted using a complete random block experimentation plan. Three repetitions were done for each treatment.

Figure 10:
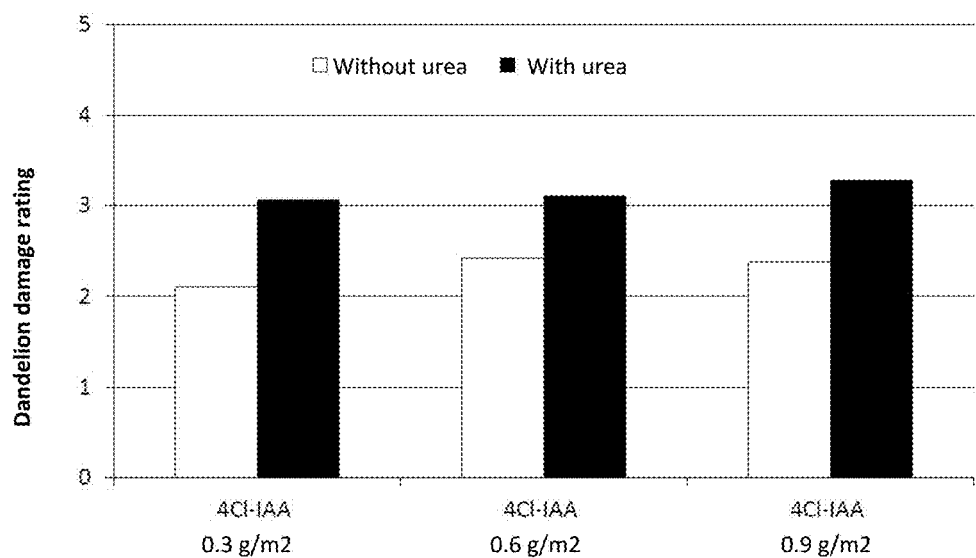
FIG. 10 Effect of urea as co-ingredient for spreading applications at different doses of 4Cl-IAA on dandelion.

Treatment: 4Cl-IAA with 10% urea and without urea applied with a spreading rate of 100 mL/m$^2$ at doses of 0.3, 0.6 and 0.9 g/m$^2$ Dependent variable: mean damage rating (from 0 to 5) of the dandelion assessed after 2 days The results are shown in FIG. 10.

Interpretation

Dandelion damage rating=control

The addition of 10% urea as co-ingredient accelerates the dandelion control efficacy perceived by the user after 48 hours. For all three studied doses, the effect of the urea is substantially the same.

Example 14

Title

Decreased presence of weeds in the turf after one or two spreading applications of 4Cl-IAA Methodology The experiment was conducted using a complete random block experimentation plan. Three repetitions were done for each treatment.

Treatment: 4Cl-IAA with a spreading rate of 100 mL/m$^2$ for an application of 0.6 g/m$^2$ with 6% urea and two applications of 0.3 g/m$^2$ with 3% urea separated by one week.

Dependent variable: Percentage of decrease in weeds estimated after 28 days from readings relative to the presence or absence of weeds using an observation grid of 100 points per square meter.

Figure 11:
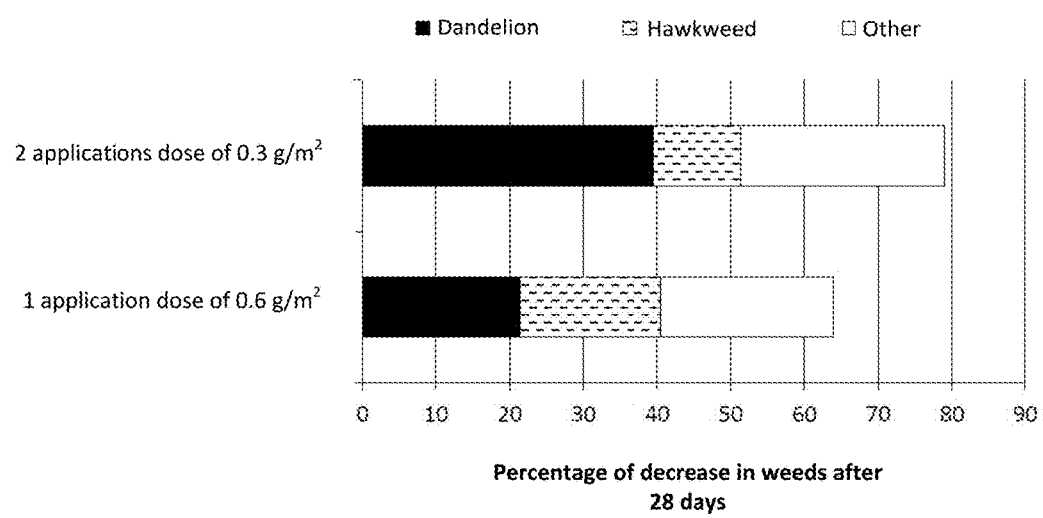
FIG. 11 Decreased presence of weeds in the turf after one or two spreading applications of 4Cl-IAA.
Figure 12:
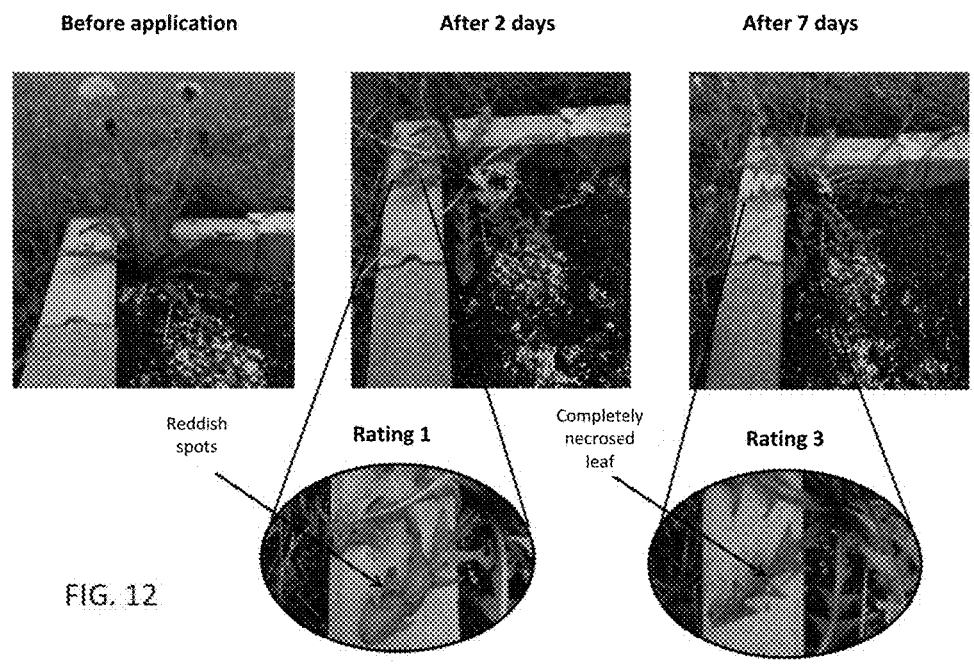
FIG. 12 Illustration of the damage rating on dandelion for a targeted application of 4Cl-IAA, without co-ingredient, after a period of 2 and 7 days with a dose of 0.03 g/plant.
Figure 13:
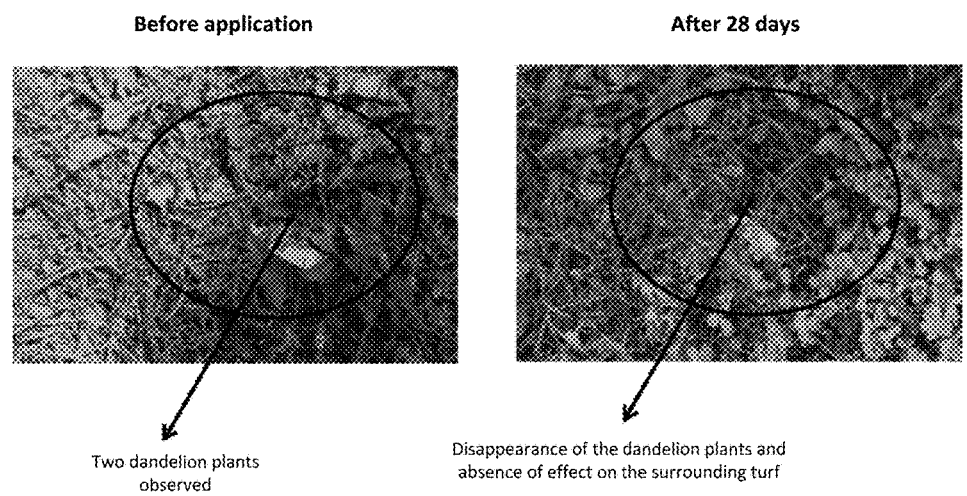
FIG. 13 Illustration of dandelion disappearance during a targeted application of 4Cl-IAA, without co-ingredient, after a period of 28 days with a dose of 0.03 g/plant.
Figure 14:
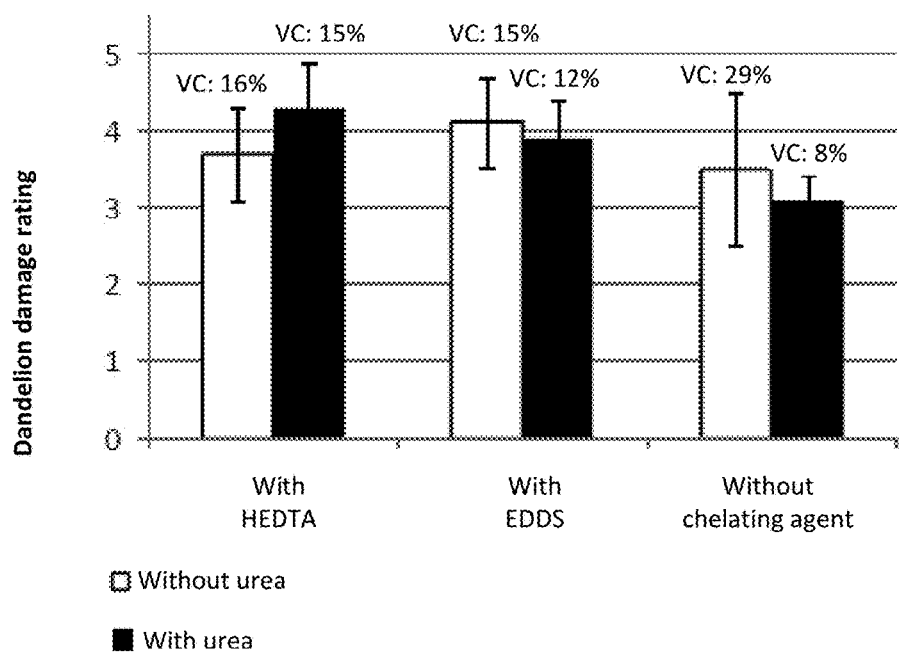
FIG. 14 Illustration of the damage rating on dandelion for a targeted application of 4Cl-IAA, without and with chelating agents (1%), 10 days after treatment with a dose of 0.0075 g/plant; and with and without urea.
Figure 15:
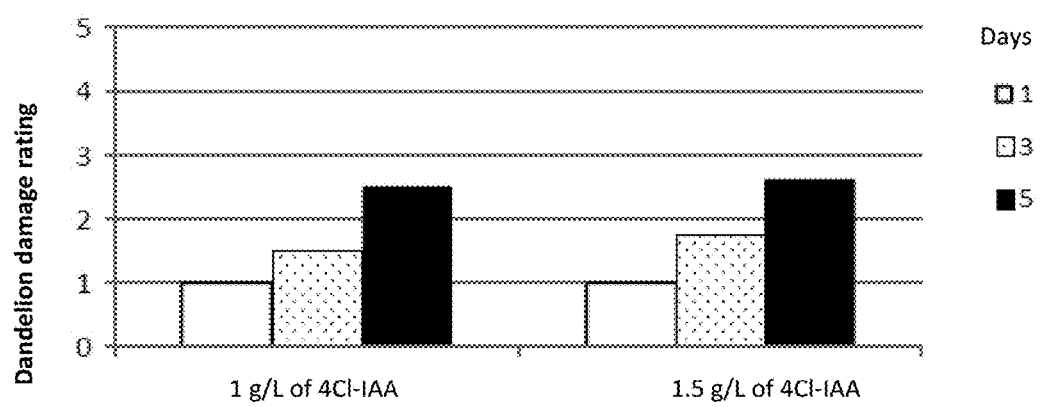
FIG. 15 Illustration of the damage rating on dandelion for a targeted application, with HEDTA (0.3 to 0.5%) and at 4Cl-IAA concentrations of 1.0 and 1.5 g/L, over a period of 1 to 5 days.

The results are shown in FIG. 11.

Interpretation

Weed disappearance=control

Both application strategies yielded decrease percentages above 60% after 28 days for different types of weeds. The strategy based on two applications yielded higher results, i.e., 79% versus 64%. Furthermore, the number of applications affects the species differently and alters the proportions of the different weeds, which may be interesting in certain situations.

Furthermore, although the preferred embodiments of the invention as described include several components and characteristics, not all of these components are necessarily essential to the invention, and they consequently must not be considered restrictively, i.e., must not be considered in such a way as to limit the scope of the present invention. It must be understood, as will be obvious for one skilled in the art, that other appropriate components and geometries and/or other possible cooperations between the latter may be used according to the present invention, without going beyond the scope of the invention.

The description must be interpreted as an illustration of the invention, and must not be considered to limit the claims. The scope of the claims must not be limited by the preferred embodiments illustrated in the examples, but must instead receive the broadest possible interpretation in accordance with the description as a whole.

The invention claimed is:

1. A method for selectively causing damage or mortality to weed, said method comprising applying on said weed an aqueous composition comprising 4-chloroindole-3-acetic acid (4Cl-IAA), in acid, salt or ester form, wherein the 4Cl-IAA, in acid, salt or ester form, is present in a concentration varying from 1.5 g/L to 40 g/L.

2. The method of claim 1, wherein said composition is spreaded on said weed.

3. The method of claim 1, wherein said composition is in the form of a viscous liquid.

4. The method according to claim 1, wherein the composition further comprises a chelating agent chosen from cyclohexanediaminetetraacetic acid (CDTA), ethylenediamine-N,N'-disuccinic acid (EDDS), EDTA, ethanol diglycine (EDG), HEDTA, methylglycinediacetic acid, glutamicadiacetic acid, trans-1,2-diaminocyclohexane-N,N,N', N'tetraacetic acid, diethylenetriaminepentaacetic acid (DTPA), iminodisuccinic acid, salts thereof, and combinations thereof.

5. The method according to claim 1, wherein the 4Cl-IAA, is present, in acid, salt or ester form, in a concentration varying from 2 g/L to 10 g/L.

6. The method according to claim 5, wherein the composition further comprises a chelating agent chosen from EDDS, EDTA, DTPA, HEDTA, salts thereof and combinations thereof.

7. The method according to claim 1, wherein said composition further comprises a co-ingredient that is a chelated or non-chelated metal, at a concentration varying from 0.1 to 5% on a weight basis.

8. The method according to claim 1, wherein said composition further comprises a co-ingredient that is sodium chloride, at a concentration varying from 1 to 36% on a weight basis.

9. The method according to claim 1, wherein said composition further comprises a co-ingredient that is urea, at a concentration varying from 1 to 50% on a weight basis.

10. The method according to claim 1, wherein said composition further comprises a co-ingredient is a fatty acid, at a concentration varying from 1 to 20% on a weight basis.

11. The method of claim 1, wherein said composition is applied on said weed and on a desirable plant for selectively causing an herbicide effect on said weed over said desirable plant.

12. The method of claim 1, wherein said composition is applied on said weed and on a desirable plant for selectively causing damage or mortality to said weed over said desirable plant.

13. The method of claim 12, wherein said composition comprises 4-chloroindole-3-acetic acid as a potassium salt.

14. The method of claim 1, wherein said composition is sprayed on said weed.

15. The method of claim 14, wherein said potassium salt of 4-chloroindole-3-acetic acid is present in a concentration varying from 2 g/L to 10 g/L.

16. The method of claim 1, wherein said composition comprises 4-chloroindole-3-acetic acid as a potassium salt.

17. The method of claim 16, wherein said potassium salt of 4-chloroindole-3-acetic acid is present in a concentration varying from 2 g/L to 10 g/L.

18. A method for selectively causing damage or mortality to weed, said method comprising applying on said weed a composition comprising (i) 4-chloroindole-3-acetic acid (4Cl-IAA), in acid, salt or ester form, and (ii) a chelating agent chosen from EDDS, EDTA, DTPA, HEDTA, salts thereof, and combinations thereof.

19. The method of claim 18, wherein the 4Cl-IAA, in acid, salt or ester form, is present in an aqueous composition in a concentration varying from 1.5 g/L to 40 g/L.

20. The method according to claim 18, wherein the 4Cl-IAA, in acid, salt or ester form, is present in said composition at a concentration varying from 1.5 g/L to 40 g/L.

21. The method according to claim 20, wherein said composition further comprises a surfactant, a preservative, a buffer or combinations thereof.

22. The method according to claim 18, wherein the 4Cl-IAA, in acid, salt or ester form, is applied at a dose greater than or equal to 0.2 g/m$^2$ and less than or equal to 0.8 g/m$^2$ for a spreading application.

23. The method of claim 20, wherein said composition comprises 4-chloroindole-3-acetic acid as a potassium salt.

24. A method for selectively causing damage or mortality to weed, said method comprising applying on said weed 4-chloroindole-3-acetic acid (4Cl-IAA), in acid, salt or ester form, wherein the 4Cl-IAA, in acid, salt or ester form, is applied at a dose greater than or equal to 0.005 g/plant and less than or equal to 0.1 g/plant for a targeted application.

25. The method of claim 24, wherein the 4Cl-IAA, in acid, salt or ester form, is applied in the form of a powdered or granular solid.

26. The method of claim 24, wherein the 4Cl-IAA is further used in combination with a chelating agent.

27. The method according to claim 26, wherein the chelating agent is chosen from cyclohexanediaminetetraacetic acid (CDTA), ethylenediamine-N,N'-disuccinic acid (EDDS), EDTA, ethanol diglycine (EDG), HEDTA, methylglycinediacetic acid, glutamicadiacetic acid, trans-1,2-diaminocyclohexane-N,N,N',N'tetraacetic acid, diethylenetriaminepentaacetic acid (DTPA), iminodisuccinic acid, salts thereof, and combinations thereof.

* * * * *